(12) United States Patent
Wich

(10) Patent No.: US 6,482,176 B1
(45) Date of Patent: Nov. 19, 2002

(54) METHOD AND DEVICE FOR CONTROLLING THE INTRODUCTION DEPTH OF AN INJECTION NEEDLE

(75) Inventor: Horst Wich, Cathedral City, CA (US)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 09/555,248

(22) PCT Filed: Nov. 24, 1997

(86) PCT No.: PCT/CH97/00448

§ 371 (c)(1),
(2), (4) Date: Oct. 2, 2000

(87) PCT Pub. No.: WO99/27986

PCT Pub. Date: Jun. 10, 1999

(51) Int. Cl.$^7$ ................................................ A61M 5/00
(52) U.S. Cl. ...................................... 604/117; 604/240
(58) Field of Search ............................... 604/117, 240, 604/242, 243, 57, 59, 60, 61

(56) References Cited

U.S. PATENT DOCUMENTS

| | | | |
|---|---|---|---|
| 2,664,086 A | | 12/1953 | Transue ...................... 128/218 |
| 3,605,744 A | | 9/1971 | Dwyer .................... 128/218 F |
| 3,677,245 A | | 7/1972 | Welch ..................... 128/218 S |
| 4,373,526 A | * | 2/1983 | Kling .......................... 128/215 |
| 4,735,611 A | | 4/1988 | Anderson et al. ............ 604/130 |
| 4,946,446 A | | 8/1990 | Vadher ........................ 604/198 |

(List continued on next page.)

FOREIGN PATENT DOCUMENTS

| | | |
|---|---|---|
| AU | 5861273 | 1/1975 |
| DE | 1022758 | 1/1958 |
| DE | 1491841 | 7/1969 |
| DE | 3638984 | 5/1988 |
| DE | 3645245 | 1/1994 |
| EP | 0268191 | 5/1988 |
| EP | 0516473 | 12/1992 |
| FR | 2700960 | 8/1994 |
| WO | WO9110460 | 7/1991 |
| WO | WO9305835 | 4/1993 |
| WO | WO9409841 | 5/1994 |

*Primary Examiner*—Sharon Kennedy
(74) *Attorney, Agent, or Firm*—Dorsey & Whitney LLP

(57) ABSTRACT

The present invention relates to a method for controlling the introduction depth of an injection needle 1 which is mounted inside a needle introduction device 17, 18 so as to be capable of axial displacement relative to an injection device 12 coupled to said needle introduction device or arranged in the same. The maximum possible run of the injection needle is set to a value H and can be shortened using a cylindrical hollow spacing member 21 which can be concentrically mounted about said injection needle 1. Since the maximum possible run H of the injection needle can be shortened using the spacing member 21, it is thus possible to obtain a penetration depth of variably range. To this end, it is possible to use a series of spacing members 21 having different axial lengths x or a spacing member which can be screwed in a front position. The cylindrical hollow spacing member 21, which is concentrically mounted about the injection needle 1, is easy to press down to the chosen introduction depth into the needle introduction device 17, 18 presently used as it is clicked in or screwed in a front position.

25 Claims, 7 Drawing Sheets

U.S. PATENT DOCUMENTS

| | | | |
|---|---|---|---|
| 4,973,318 A | | 11/1990 | Holm et al. .................. 604/208 |
| 5,092,376 A | * | 3/1992 | Blankenship et al. ........ 604/117 |
| 5,092,842 A | | 3/1992 | Bechtold et al. ............. 604/135 |
| 5,114,406 A | | 5/1992 | Gabriel et al. ............... 604/136 |
| 5,141,496 A | * | 8/1992 | Dalto et al. .................. 604/117 |
| 5,209,739 A | | 5/1993 | Talalay ........................ 604/195 |
| 5,244,465 A | | 9/1993 | Michel ......................... 604/218 |
| 5,292,314 A | | 3/1994 | D'Alessio et al. ........... 604/198 |
| 5,338,311 A | | 8/1994 | Mahurkar .................... 604/195 |
| 5,368,046 A | * | 11/1994 | Scarfone et al. ............. 128/754 |
| 5,514,097 A | | 5/1996 | Knauer ........................ 604/136 |
| 5,527,294 A | | 6/1996 | Weatherford et al. ........ 604/198 |
| 5,540,664 A | | 7/1996 | Wyrick ........................ 604/136 |
| 5,549,558 A | | 8/1996 | Martin ......................... 604/110 |
| 5,573,510 A | | 11/1996 | Isaacson ...................... 604/158 |
| 5,599,309 A | * | 2/1997 | Marshall et al. ............. 604/136 |
| 5,643,214 A | | 7/1997 | Marshall et al. ............. 604/134 |
| 5,658,259 A | | 8/1997 | Pearson et al. .............. 604/232 |
| 5,779,677 A | | 7/1998 | Frezza ......................... 604/134 |
| 5,873,856 A | | 2/1999 | Hiertman et al. ............ 604/117 |
| 5,944,700 A | * | 8/1999 | Nguyen et al. .............. 604/263 |

* cited by examiner

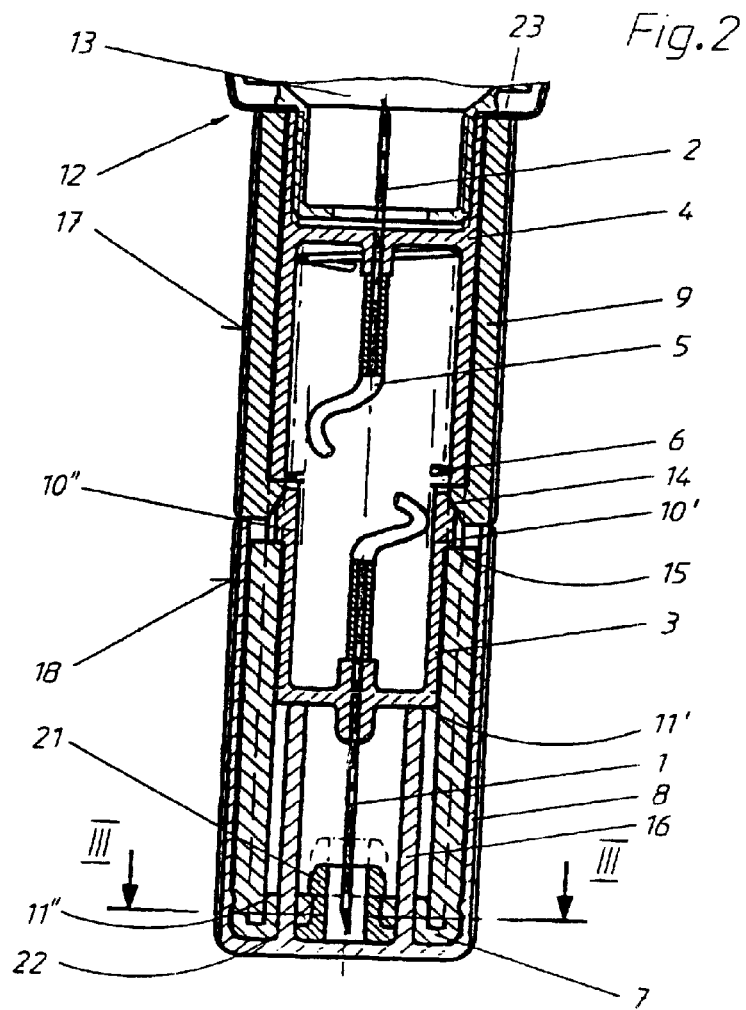
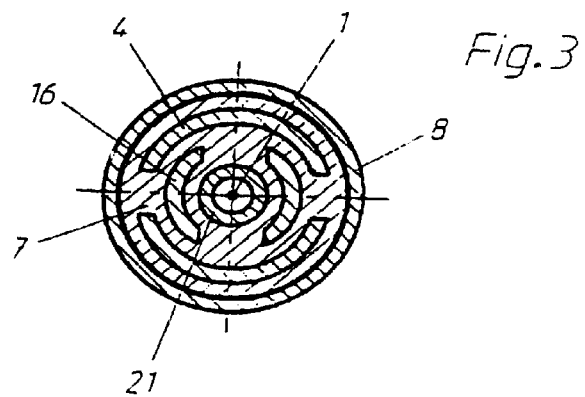

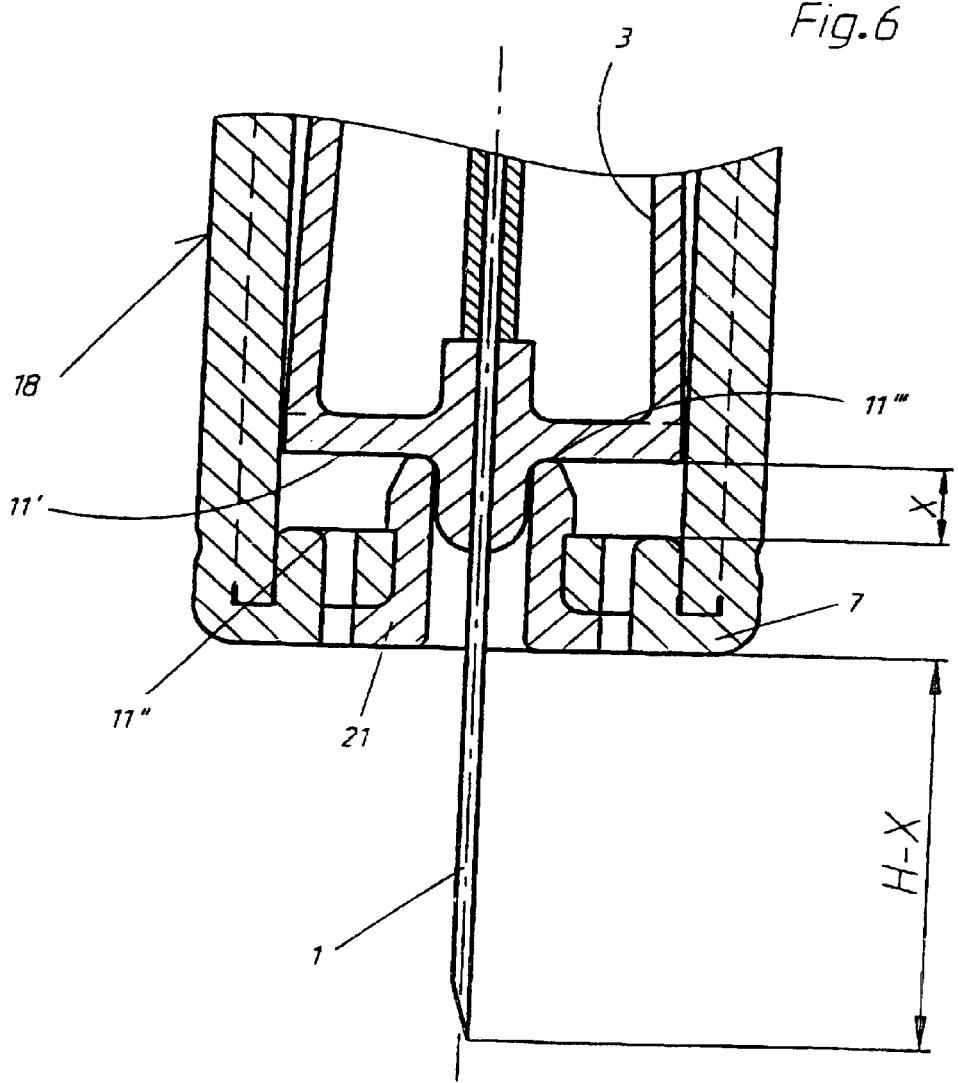

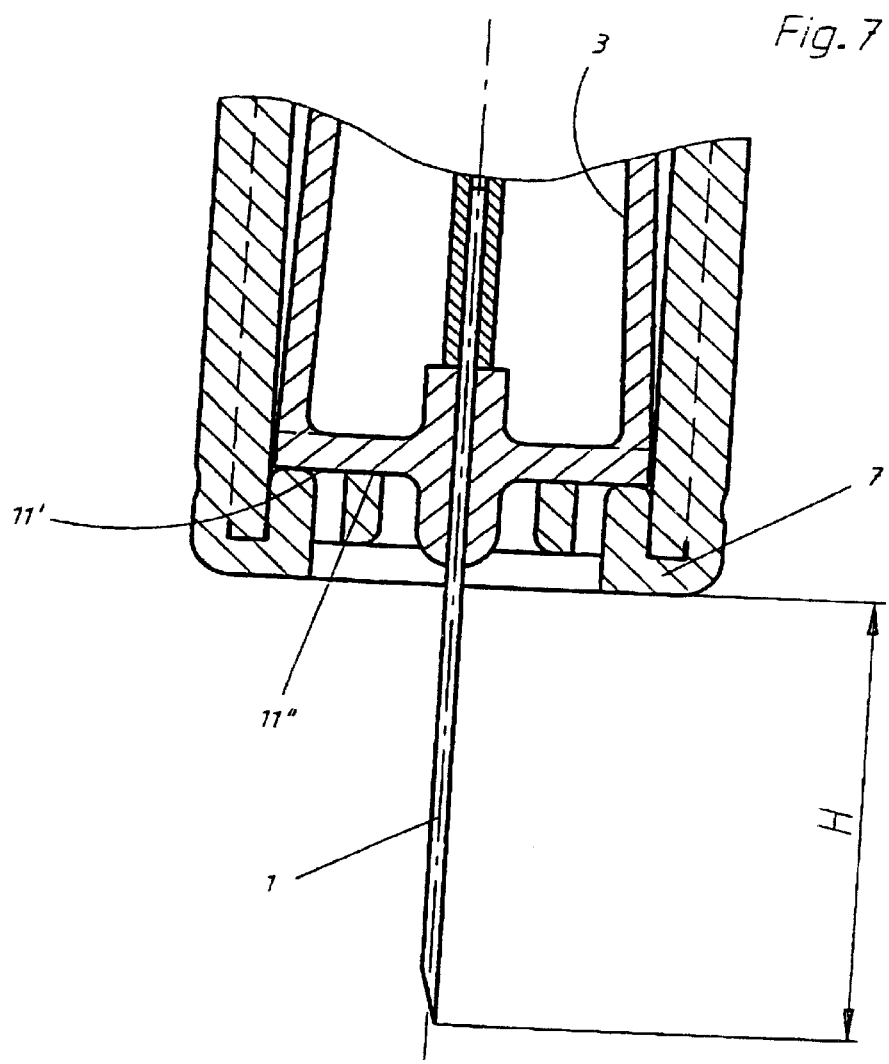

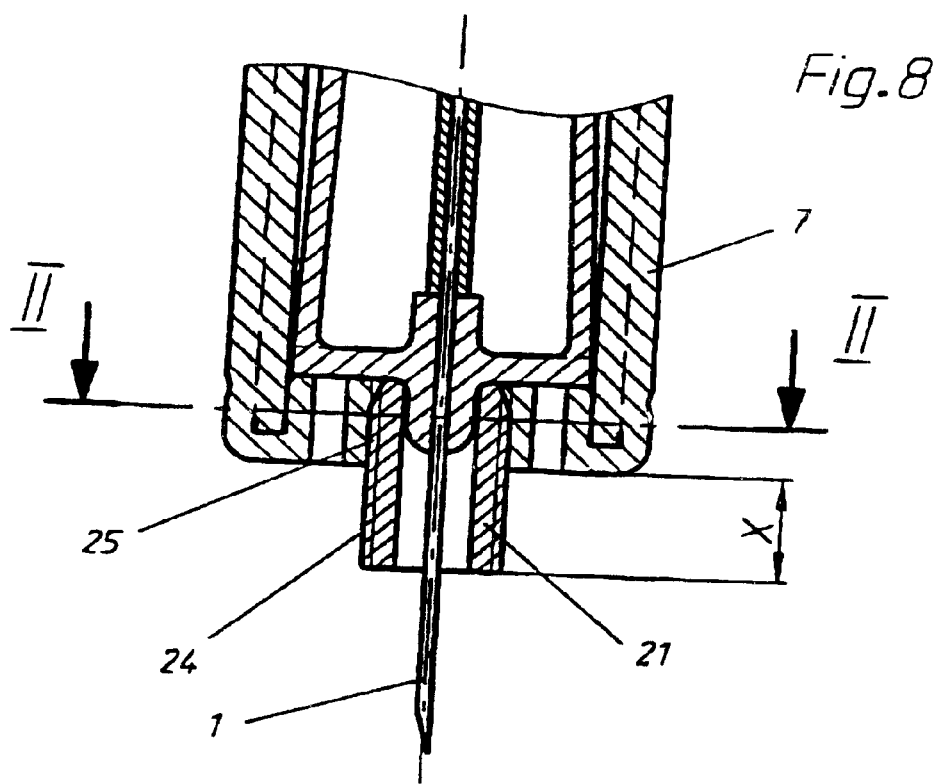
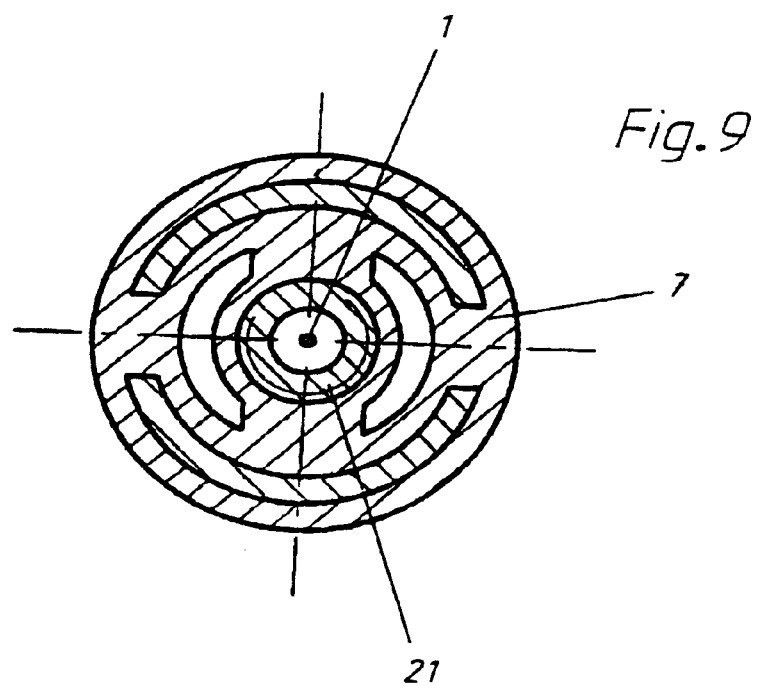

METHOD AND DEVICE FOR CONTROLLING THE INTRODUCTION DEPTH OF AN INJECTION NEEDLE

This application claims the priority of PCT application PCT/CH97/00448, filed Nov. 27, 1997, which is incorporated herein by reference.

BACKGROUND OF THE INVENTION

The invention relates to a method for controlling the introduction depth of an injection needle in accordance with the preamble of claim 1 and to an apparatus for implementing this method as it reads from claim 3.

With conventional injection devices there is often the problem that the operator—the nurse or the patient—is unable to control, unaided, the introduction depth of the needle. Where a slender child is concerned, in comparison to a corpulent grown-up, a substantially shorter introduction depth suffices. If the injection needle is inserted unnecessarily deep in the tissue skin, pain materializes which is avoidable. In particular, in the case of patients who often have to endure frequent injections, e.g. diabetics, this leads to an aversion to or even a fear of the next injection.

SUMMARY OF THE INVENTION

The present invention is thus based on the object of providing a method and an apparatus for controlling the introduction depth of an injection needle by means of which the user is able to set the optimal introduction depth for the nature of the skin tissue concerned.

The invention achieves this desired object by providing a method, comprising the features of the characterizing part of the independent claim 1, and an apparatus, comprising the features of the characterizing part of the independent claim 3.

Due to the shortening of the maximum possible travel H of the injection needle by a spacer, it is possible to vary the introduction depth. This may be done either by a series of spacers differing in axial length x or by a frontal screw-on type spacer. The hollow-cylindrical spacer, arranged concentrically about the injection needle, may be simply snapped or clicked into the needle introduction device used, or be set by frontal screw-mounting to the desired introduction depth.

The needle introduction device is configured either as a separate unit for coupling to a conventional injection device or it may be integrated in the injection device.

When no spacer is clicked into the needle introduction device, or if the frontal screw-mounting spacer is in its resting position, then the maximum possible travel of the injection needle is permitted to thus attain the deepest introduction depth. If a spacer is click-mounted or screw-mounted into the travel of the injection needle, then the maximum travel H is shortened by the amount x and a shorter introduction depth results.

In a preferred embodiment of the invention, the needle introduction device is a separate unit which can be coupled to a conventional injection device, this unit comprising a rear longitudinal part including a piercing needle (which can be coupled to the injection device) and a front longitudinal part including an injection needle for delivery of the fluid into the tissue skin or subcutaneously. Provided between the piercing needle and the injection needle is a flexible connection.

The needle introduction device is connectable via the piercing needle to the pen cartridge of the injection device so that the fluid to be delivered into the tissue skin or subcutaneously is injectable via the injection needle and the procedure of introducing the injection needle into the tissue skin or subcutaneously automatically occurs upon manual activation of a control element of the needle introduction device, accommodated in the rear longitudinal part, and the fluid can be administered via the injection device.

Serving as the control element is an initiator sleeve arranged longitudinally shiftable on a piercing needle mount mounting the piercing needle and cooperates with an injection needle mount, likewise longitudinally shiftable in a stopper sleeve, mounting the injection needle.

Introducing the injection needle into the tissue skin or subcutaneously after manual activation of the initiator sleeve occurs in that the injection needle mount together with the injection needle is automatically moved by means of the force of a spring in the direction of the tissue skin. Following automatic introduction of the injection needle into the tissue skin or subcutaneously, the user is able to administer the dose of fluid required by means of the conventional injection device.

The apparatus in accordance with the invention has the salient advantage that it offers highly reliable assurance in controlling the introduction depth of the injection needle into the tissue skin or subcutaneously.

Further advantageous aspects of the invention read from the dependent claims.

BRIEF DESCRIPTION OF THE DRAWINGS

An example embodiment of the invention is illustrated in the Figures in which:

FIG. 2: is a longitudinal section through the apparatus in accordance with FIG. 1 after insertion of the spacer;

FIG. 3: is a cross-section taken along the line III—III as shown in FIG. 2;

FIG. 6: is a longitudinal section through the apparatus in accordance with FIG. 2 (including spacer) after actuating the travel of the needle introduction device;

FIG. 7: is a longitudinal section through the apparatus in accordance with FIG. 1 (without spacer) after actuating the travel of the needle introduction device;

FIG. 8: is a partial longitudinal section through an apparatus in accordance with the invention including a screw-mounting spacer; and FIG. 9: is a cross-section taken along the line II—II as shown in FIG. 8.

DETAILED DESCRIPTION

Figure 1:
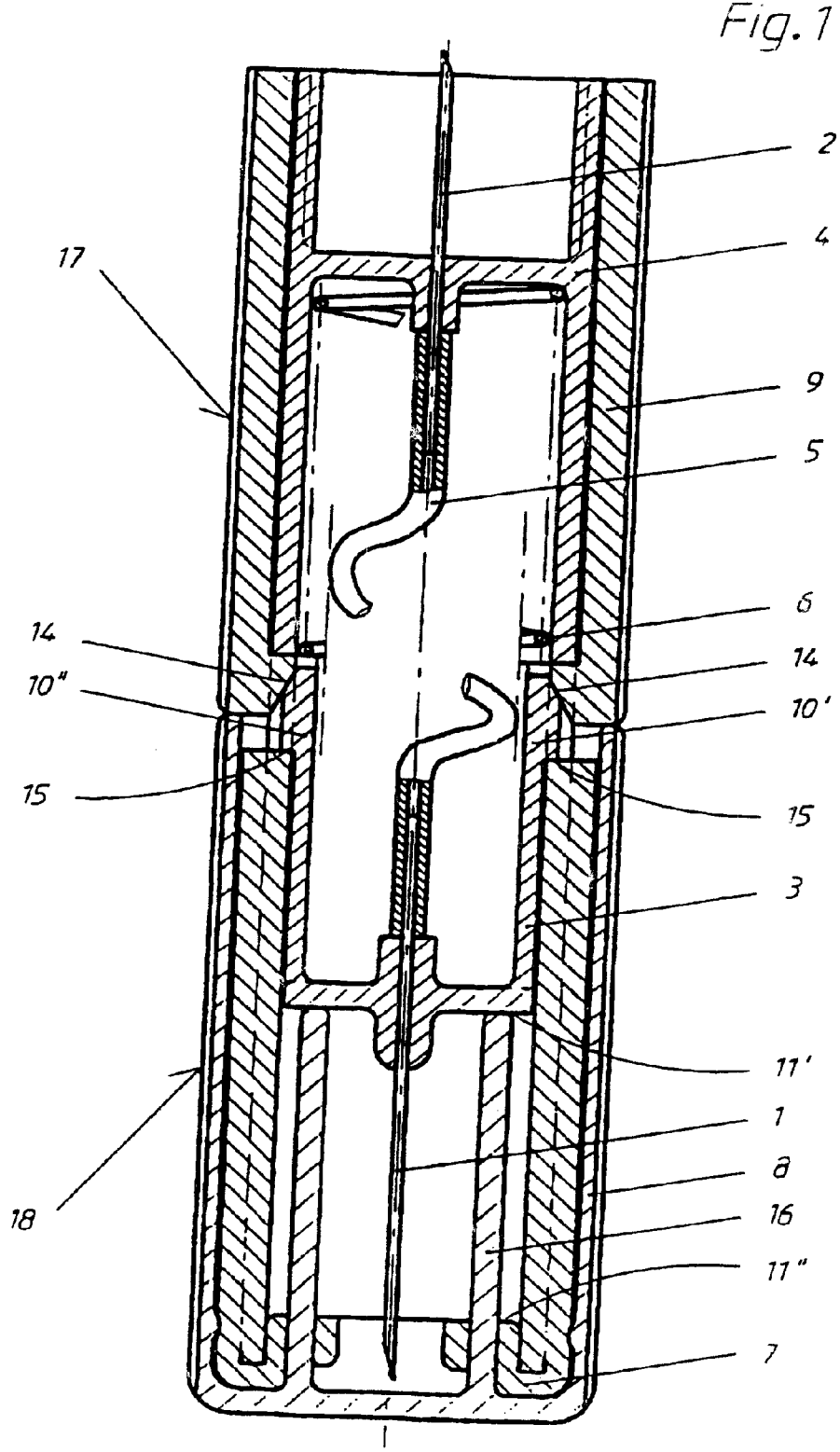
FIG. 1: is a longitudinal section through an apparatus in accordance with the invention prior to insertion of the spacer, the needle introduction device being in the starting position or resting position.

Referring now to FIG. 1 there is illustrated a needle introduction device 17, 18 for injecting a fluid. The needle introduction device 17, 18 comprises substantially a rear longitudinal part 17, including a piercing needle 2, and a front longitudinal part 18, including an injection needle 1 for delivering the fluid into the tissue skin or subcutaneously, as well as a flexible connection 5 between the piercing needle 2 and the injection needle 1.

The needle introduction device 17, 18 can be coupled to the conventional injection device 12, for example, by a screw lock or by a latch cam mount 23 (FIG. 2). Via the piercing needle 2 provided at one end of the needle introduction device 17, 18, the needle introduction device 17, 18 is connected to the pen cartridge 13 of the conventional injection device 12. Via the injection needle 1 provided at the other end of the needle introduction device 17, 18, the fluid is injectable into the tissue skin or subcutaneously. Provided between the piercing needle 2 and the injection needle 1 is the flexible connection 5 for fluid transport. The procedure of introducing the injection needle 1 into the tissue skin or subcutaneously occurs automatically after manual activation of a control element in the form of the initiator sleeve 9 of the needle introduction device 17, 18, after which, the fluid can be administered via the conventional injection device 12. The initiator sleeve 9 is arranged longitudinally shiftable on the piercing needle mount 4 mounting the piercing needle 2 and cooperates with the injection needle mount 3, likewise longitudinally shiftable in the piercing needle mount 4 and in the stopper sleeve 7, said injection needle mount 3 mounting the injection needle 1. Introduction of the injection needle 1 into the tissue skin or subcutaneously occurs after manual activation of the initiator sleeve 9 by means of the force of the spring 6, in that the injection needle mount 3 together with the injection needle 1 is automatically moved against the tissue skin. In this way, the spring 6 is supported at its one end by the fixed piercing needle mount 4 and moves with its other end the injection needle mount 3 including the injection needle 1 in the direction of the tissue skin into which the injection needle 1 is automatically introduced. The cooperation of the initiator sleeve 9 and the injection needle mount 3 during manual activation of the initiator sleeve 9 occurs via the bevel tapers 14 by which the injection needle mount 3 is squeezed diametrically to thus defeat the lock consisting of the stopper 15 of the stopper sleeve 7 and the mounting cams 10', 10" of the injection needle mount 3 and thereby enabling the spring 6 to develop its urging effect. The injection needle mount 3 together with the injection needle 1 is automatically moved after manual activation of the initiator sleeve 9 by means of the force of spring 6 so long in the direction of the tissue skin until the face 11' of the injection needle mount 3 comes up against the face 11" of the stopper sleeve 7. On completion of injection, the injection needle mount 3 with the injection needle 1 is manually retractable by means of the safety cap 8, surrounding the stopper sleeve 7, against the force of the spring 6 until the lock consisting of the stopper 15 of the stopper sleeve 7 and the mounting cams 10', 10" of the injection needle mount 3 is again effective. At the same time, the initiator sleeve 9 is longitudinally shiftable by means of the bevel tapers 14 in the direction of the conventional injection device 12 by the safety cap 8 so that the initiator sleeve 9 is retracted into the starting position or resting position and is ready for a repeat manual activation. For retracting the injection needle mount 3 with the injection needle 1 by means of the safety cap 8, the latter is provided in its interior with a protective cylinder 16 surrounding and protecting the injection needle 1. The protective cylinder 16 also has the function that its open end contacts the face 11' of the injection needle mount 3 and thus, when the safety cap 8 is shifted into the condition protecting the injection needle 1, it retracts the injection needle mount 3 together with the injection needle as well as the initiator sleeve 9 into the starting position.

The functioning of the needle introduction device 17, 18 in accordance with the invention will now be described:

The needle introduction device 17, 18 is mechanically coupled to the conventional injection device 12 by e.g. a screw lock or by a latch cam mount or similar, the piercing needle 2 piercing the pen cartridge septum to ensure that the fluid to be injected communicates with the needle introduction device. The user then brings the latter to the preferred tissue skin location before then activating the initiator sleeve 9 by pushing it longitudinally down in the direction of the tissue skin until the lock consisting of the stopper 15 of the stopper sleeve 7 and the mounting cams 10', 10" of the injection needle mount 3 is defeated. This enables the spring 6 to develop its force and automatically urge the injection needle mount 3 with the injection needle 1 in the direction of the tissue skin until the face 11' of the injection needle mount 3 comes up against the face 11" of the stopper sleeve 7, as a result of which the injection needle 1 is automatically introduced into the tissue skin. Now, the user is able to deliver the dose of fluid to be administered by means of the conventional injection device 12. On completion of injection, the injection needle mount 3 with the injection needle 1 is by means of safety cap 8, surrounding the stopper sleeve 7, manually retractable against the force of the spring 6. The lock is again effective and, at the same time, the initiator sleeve 9 returns to its starting position or resting position.

The piercing needle mount 3 may be preferably slotted in the region of the bevel tapers 14 to improve its elasticity when it is squeezed in cooperating with the initiator sleeve 9 during activation to defeat the lock.

Referring now to FIGS. 2 and 3, there is illustrated the needle introduction device 17, 18 in which a hollow-cylindrical spacer 21 is click-mounted concentrically about the injection needle 1 in the front longitudinal part 18 where it is secured in place. For this purpose, the spacer 21 comprises a peripheral undercut 22. Once fitted, the spacer 21, which is preferably made of a plastics material, remains in the needle introduction device 17, 18 provided as an instrument for once-only use and is thus disposed of along with the former.

Figure 4:
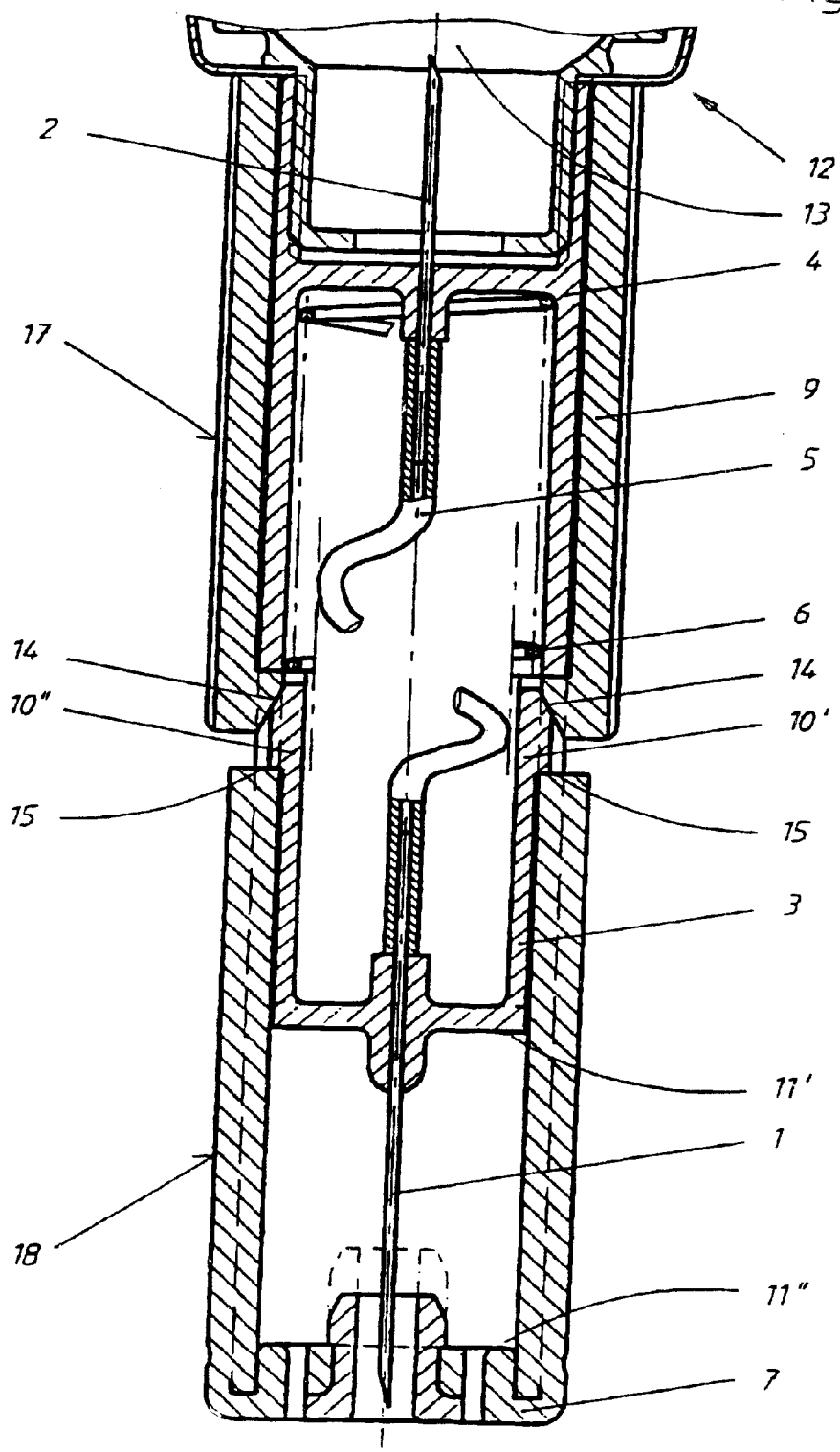
FIG. 4: is a longitudinal section through the apparatus in accordance with FIG. 2 in the safety release position after removal of the safety cap.

FIG. 4 illustrates a longitudinal section of the needle introduction device 17, 18 in the released condition after removal of the safety cap 8. Except for this safety cap 8, FIG. 4 is substantially identical to FIG. 2 The reference numerals are identical in both figures.

Figure 5:
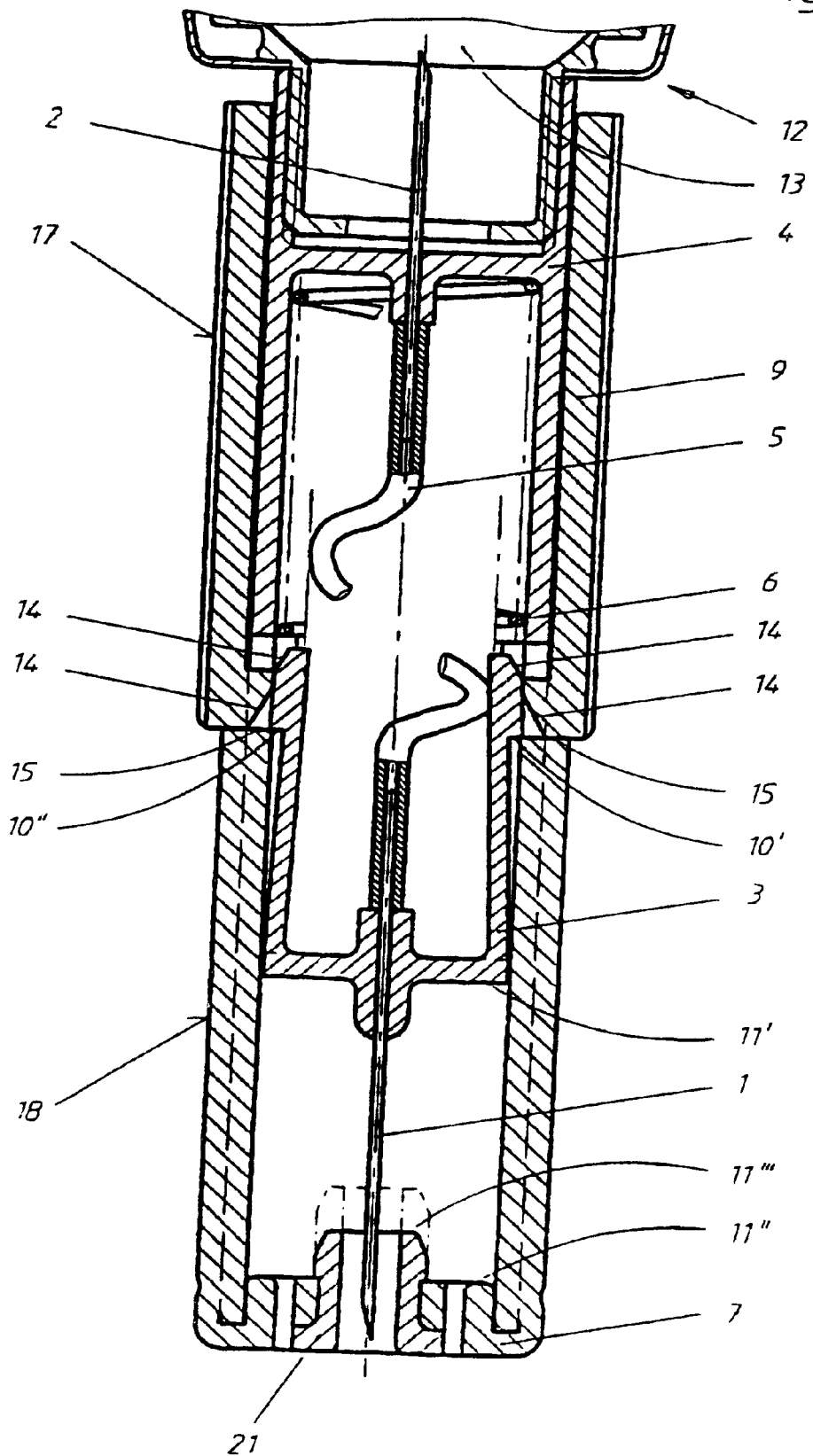
FIG. 5: is a longitudinal section through the apparatus in accordance with FIG. 2 after manual activation of the initiator sleeve.

FIG. 5 shows a longitudinal section of the needle introduction device 17, 18 after manual activation of the initiator sleeve 9. It is evident from this figure how, directly after defeating the lock, consisting of the stopper 15 of the stopper sleeve 7 and the mounting cams 10', 10" of the injection needle mount 3, due to cooperation of the bevel tapers 14 of the injection needle mount 3 and initiator sleeve 9, the injection needle mount 3 is flexibly squeezed so that the spring 6 can develop its force and automatic introduction of the injection needle 1 in the tissue skin or subcutaneously can commence.

In contrast to the needle introduction device having no inserted spacer 21, in this case, the injection needle mount 3 can be advanced only up to the face 11'''. The result of this is that the introduction depth is of varying shortness. As evident from FIGS. 6/7, the face 11' of the injection needle mount 3 abuts against the face 11" of the stopper sleeve 7 earlier due to insertion of the spacer 21 (FIG. 6), i.e. by the distance x between the face 11''' and face 11". Accordingly, with an inserted spacer 21 (FIG. 6), the introduction depth is H-x, as compared to the situation shown in FIG. 7 without spacer where the introduction depth is H.

Finally, FIGS. 8 and 9 illustrate a further embodiment of the invention in which the spacer 21 comprising a male thread 24 is frontally screw-mounted into the female thread 25 of the stopper sleeve 7 to thus make a variable shortening of the needle travel possible.

The apparatus in accordance with the invention is applicable for administering medications preferably. However, it may also be used in all applications in which a fluid is to be injected into a body and the injection needle is required to be inserted with automatic control of the introduction depth of the injection needle.

What is claimed is:

1. A method for controlling the introduction depth of an injection needle comprising:
    arranging the needle in a needle introduction device, wherein the needle is axially movable with respect to said needle introduction device, the needle's maximum travel amounting to the value H; and
    adjusting the maximum possible travel H of said injection needle by manipulating a hollow-cylindrical spacer securable generally concentrically about said injection needle.

2. The method as set forth in claim 1, wherein the hollow cylindrical spacer has an axial length x and thus the travel of said injection needle may be shortened to the value H-x.

3. An apparatus for controlling the introduction depth of an injection needle, comprising: a needle introduction device; an injection needle, said injection needle being arranged within said needle introduction device and axially movable relative to an injection device, said injection device being coupled to or comprising the needle introduction device, whereby the maximum travel of said injection needle amounts to the value H; and a hollow-cylindrical spacer, said spacer being insertable into the needle introduction device and securable concentrically about said injection needle, said spacer being used to shorten the maximum travel of said injection needle.

4. The apparatus as set forth in claim 3, wherein said needle introduction device comprises a snap-action or click mounting in which said spacer can be snapped or clicked into place.

5. The apparatus as set forth in claim 3, wherein said needle introduction device comprises a screw-mount in which said spacer comprising a male thread can be screwed frontally into a female thread of said needle introduction device.

6. The apparatus as set forth in claim 3, wherein said needle introduction device further comprises the following components:
    a) a rear longitudinal part including a piercing needle for coupling to said injection device;
    b) a front longitudinal part containing said injection needle, said injection needle being used for delivering a fluid into the tissue skin or subcutaneously; and
    c) a flexible connection between said piercing needle and said injection needle.

7. The apparatus as set forth in claim 3, wherein said needle introduction device is connectable via a piercing needle to a pen cartridge of said injection device, that via said injection needle a fluid to be delivered is injectable into the tissue skin or subcutaneously and that the procedure of introducing said injection needle into the tissue skin or subcutaneously occurs automatically following manual activation of a needle introduction device control element accommodated in a rear longitudinal part of said needle introduction device and said fluid can be administered via said injection device.

8. The apparatus as set forth in claim 7, wherein said control element is an initiator sleeve arranged longitudinally shiftable on a piercing needle mount mounting said piercing needle and the initiator sleeve cooperates with an injection needle mount mounting said injection needle, the injection needle mount, in a stopper sleeve, being longitudinally shiftable too.

9. The apparatus as set forth in claim 3, wherein introducing said injection needle into the tissue skin or subcutaneously occurs following manual activation of an initiator sleeve by means of the force of a spring.

10. The apparatus as set forth in claim 3, wherein a spring is supported at its one end by a fixed piercing needle mount and moves by its other end an injection needle mount including said injection needle in the direction of tissue skin and introduces said injection needle automatically into the skin.

11. The apparatus as set forth in claim 3, wherein cooperation of an initiator sleeve and an injection needle mount in manual activation of said initiator sleeve occurs via one or more bevel tapers by which said injection needle mount is squeezed diametrically to thus defeat a lock consisting of one or more stoppers of a stopper sleeve and one or more mounting cams of said injection needle mount, thereby enabling a spring to develop its urging effect.

12. The apparatus as set forth in claim 3, wherein, after manual activation of an initiator sleeve, an injection needle mount together with said injection needle is automatically moved in the direction of a tissue skin by the force of a spring until a face of said injection needle mount comes up against a face of a stopper sleeve or a face of said spacer.

13. The apparatus as set forth in claim 3, wherein, on completion of injection, an injection needle mount with said injection needle is manually retractable by means of a safety cap, said cap surrounding a stopper sleeve and being applied against the force of a spring until a lock consisting of one or more stoppers of said stopper sleeve and one or more mounting cams of said injection needle mount is again effective and, at the same time, an initiator sleeve is longitudinally shiftable by means of one or more bevel tapers in the direction of said injection device so that said initiator sleeve is ready for a repeat manual activation.

14. The apparatus as set forth in claim 3, wherein said needle introduction device is coupled to said injection device by a screw lock or by a latch cam mount.

15. The apparatus as set forth in claim 3, wherein provided between a piercing needle and said injection needle is a flexible connection for fluid transport.

16. The apparatus as set forth in claim 3, further comprising a safety cap, said cap having in its interior a protective cylinder surrounding said injection needle.

17. An apparatus for controlling the introduction depth of an injection needle, the apparatus comprising a needle introduction device said introduction device comprising:
    an initiator sleeve comprising one or more upper bevel tapers, said initiator sleeve being axially movable with respect to the introduction device;
    a stopper sleeve comprising one or more stopper surfaces;
    an injection needle mount comprising an injection needle, a face, one or more mounting cams, and one or more lower bevel tapers, said injection needle being perpendicularly mounted in said face, said mounting cams and said stopper surfaces engaging to form a lock;
    no more than one helical spring, said spring being free to move the injection needle mount axially within the stopper sleeve upon a disengagement of said lock, said disengagement being brought about by the manual activation of said initiator sleeve whereby the upper bevel tapers are forced against the lower bevel tapers, diametrically squeezing the lower bevel tapers and causing the mounting cams to become disengaged from said stopper surfaces;

a first end, said first end being the surface of the introduction device to make patient contact during an injection; and a spacer, said spacer being capable of being located concentrically about the injection needle and inserted into the first end, the spacer being used to adjust the introduction depth of the injection needle by adjusting the length of travel available to the injection needle mount.

18. The needle introduction device of claim 17 wherein the spacer comprises a snap-action or click mounting whereby the spacer can be snapped or clicked into its location in the first end.

19. The needle introduction device of claim 17 wherein the first end of the needle introduction device comprises a female threaded screw-mount in which the spacer comprising a male thread can be screwed frontally into its location in the first end.

20. The needle introduction device of claim 17 further comprising a piercing needle mount located within the initiator sleeve, said piercing needle mount having a face and a piercing needle, said piercing needle being perpendicularly mounted in the face of the piercing needle mount.

21. The needle introduction device of claim 20 further comprising a flexible connection having a first end and a second end, said first end being connected to the injection needle, said second end being connected to the piercing needle, the flexible connection being used for fluid transport.

22. The needle introduction device of claim 17 further comprising a safety cap having a protective cylinder with an open end, said cylinder being located concentrically about the injection needle.

23. The needle introduction device of claim 22 wherein the open end of the cylinder is used to press against the face of the injection needle mount to move the injection needle mount back to the point where the lock engages between the stopper surfaces and the mounting cams.

24. The needle introduction device of claim 17 further comprising a second end, said second end being opposite the first end and having a screw lock or a latch cam mount for coupling the needle introduction device to an injection device.

25. The apparatus of claim 17 further comprising an injection device, the injection device comprising or being coupled to the needle introduction device.

* * * * *